United States Patent
Viola et al.

(10) Patent No.: US 11,186,541 B2
(45) Date of Patent: Nov. 30, 2021

(54) POTENT INHIBITORS OF ASPARTATE N-ACETYL-TRANSFERASE FOR THE TREATMENT OF CANAVAN DISEASE

(71) Applicant: The University of Toledo, Toledo, OH (US)

(72) Inventors: Ronald E. Viola, Toledo, OH (US); Bharani Thangavelu, Toledo, OH (US); Vinay Mutthamsetty, Toledo, OH (US); Qinzhe Wang, Toledo, OH (US)

(73) Assignee: The University of Toledo, Toledo, OH (US)

( * ) Notice: Subject to any disclaimer, the term of this patent is extended or adjusted under 35 U.S.C. 154(b) by 436 days.

(21) Appl. No.: 16/088,248

(22) PCT Filed: Mar. 23, 2017

(86) PCT No.: PCT/US2017/023775
§ 371 (c)(1),
(2) Date: Sep. 25, 2018

(87) PCT Pub. No.: WO2017/172476
PCT Pub. Date: Oct. 5, 2017

(65) Prior Publication Data
US 2020/0270202 A1    Aug. 27, 2020

Related U.S. Application Data

(60) Provisional application No. 62/313,902, filed on Mar. 28, 2016.

(51) Int. Cl.
*C07C 233/51* (2006.01)
*C07C 229/36* (2006.01)
*C07C 269/06* (2006.01)
*C07C 271/22* (2006.01)

(52) U.S. Cl.
CPC .......... *C07C 233/51* (2013.01); *C07C 229/36* (2013.01); *C07C 269/06* (2013.01); *C07C 271/22* (2013.01)

(58) Field of Classification Search
CPC ............................ C07C 233/51; C07C 229/36
See application file for complete search history.

(56) References Cited

U.S. PATENT DOCUMENTS 4,701,210 A * 10/1987 Tanaka ................... A01N 39/00
                                                                   504/322
8,329,159 B2 * 12/2012 Belema ................... C07F 5/025
                                                                   424/85.2
10,449,168 B2 * 10/2019 Viola .................... A61K 31/198

OTHER PUBLICATIONS

Kim et al (2010): STN International CAPLUS database, (Columbus, Ohio), Accession No. 2010: 786423.*
Ranganathan et al (1993): STN International CAPLUS database, (Columbus, Ohio), Accession No. 1993: 449870.*
Ben-Ishai et al (1977): STN International CAPLUS database, (Columbus, Ohio), Accession No. 1977: 171841.*
McCall et al (2014): STN International CAPLUS database, (Columbus, Ohio), Accession No. 2014: 1707499.*
Comte et al. (2002): STN International CAPLUS database, (Columbus, Ohio), Accession No. 2002: 520501.*
King et al. (1998): STN International CAPLUS database, (Columbus, Ohio), Accession No. 1998: 684457.*

* cited by examiner

*Primary Examiner* — Golam M Shameem
(74) *Attorney, Agent, or Firm* — MacMillan, Sobanski & Todd, LLC

(57) ABSTRACT

Compounds, compositions, and methods for the treatment of Canavan disease are described.

12 Claims, 10 Drawing Sheets

| Table 1: Summary of Compound Library Screening against ANAT ||||| 
|---|---|---|---|---|
| Library | compounds | moderate inhibitors* | strong inhibitors# | Most potent ($K_i$) |
| Amino acids | 96 | 3 | 0 | N-chloroacetyl-L-aspartic acid ($K_i$ = 200 µM) |
| Metabolites | 96 | 13 | 0 | 2-bromofumarate ($K_i$ = 367 µM) |
| Amino acids II | 64 | 1 | 0 | N-alanyl-L-aspartic acid ($K_i$ = 1.6 mM) |
| Constrained analogs | 77 | 5 | 1 | N-carbobenzyloxy-L-aspartic acid ($K_i$ = 17 µM) |
| Synthesized dioic acids | 68 | 24 | 6 | N-carbobenzyloxy-L-glutamic acid ($K_i$ = 12 µM) N-(1-oxo-3-phenylpropyl)-L-aspartic acid ($K_i$ = 31 µM) |
| TOTAL | 401 | 46 | 7 | |
| Hit rate | | 11.5% | 1.7% | |

\* at least 50% inhibition when tested at 2 mM concentration compounds with $K_i$ values less than 200 µM

FIG. 2 - Table 1

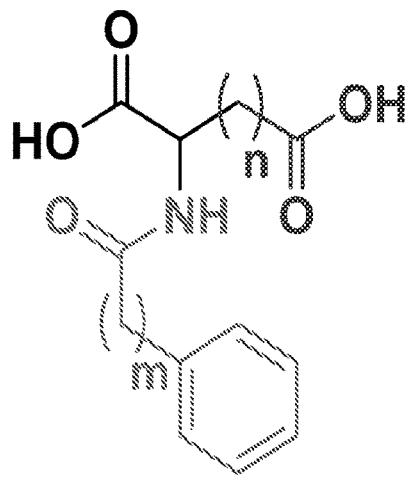

FIG. 3

Table 2: N-Acylation derivatives of aminomalonic, aspartic, glutamic, and aminoadipic acids

| No. | | m | linker | R group | $K_i$ (mM) |
|---|---|---|---|---|---|
| 1 | aminomalonate derivative (n=0) | 2 | acyl | 3-phenylpropanoyl | 1.4 ± 0.2 |
| 2 | aspartate derivatives (n = 1) | 0 | acyl | benzoyl | >2 |
| 3 | | 1 | acyl | 2-phenylacetyl | 0.46 ± 0.08 |
| 4 | | 2 | acyl | 3-phenylpropanoyl* | 0.031 ± 0.002 |
| 5 | | 2 | ester | benzylcarbanoyl* | 0.017 ± 0.002 |
| 6 | | 3 | acyl | 4-phenylbutanoyl | 0.20 ± 0.02 |
| 7 | glutamate derivatives (n = 2) | 0 | acyl | benzoyl | 0.13 ± 0.01 |
| 8 | | 1 | acyl | 2-phenylacetyl | 0.25 ± 0.03 |
| 9 | | 2 | acyl | 3-phenylpropanoyl* | 0.038 ± 0.002 |
| 10 | | 2 | ester | benzylcarbanoyl* | 0.012 ± 0.001 |
| 11 | | 3 | acyl | 4-phenylbutanoyl | 0.61 ± 0.12 |
| 12 | 2-aminoadipate derivatives (n = 3) | 0 | acyl | benzoyl | 1.60 ± 0.34 |
| 13 | | 1 | acyl | 2-phenylacetyl | 1.16 ± 0.24 |
| 14 | | 2 | acyl | 3-phenylpropanoyl | 2.90 ± 0.30 |
| 15 | | 2 | ester | benzylcarbanoyl | 2.35 ± 0.29 |
| 16 | | 3 | acyl | 4-phenylbutanoyl | 0.74 ± 0.17 |

* Substitutions shown in red indicate the best inhibitors in this compound class

FIG. 4A - Table 2

| Table 2B: Substrate Analog Inhibitors of ANAT | K$_i$ (mM) |
|---|---|
| N-[(benzyloxy)carbonyl]-L-aspartic acid | 0.017 ± 0.003 |
| N-chloroacetyl-L-aspartic acid | 0.20 ± 0.04 |
| N-(t-butoxycarbonyl)-L-aspartic acid | 0.21 ± 0.01 |
| N-[(4-methylphenyl)sulfonyl]-L-proline | 1.17 ± 0.23 |
| N-methyl-DL-aspartic acid | 1.44 ± 0.20 |
| N-alanyl-L-aspartic acid | 1.59 ± 0.24 |
| 2-(3-chloro-6-oxopyridazin-1(6H)-yl)acetic acid | 1.60 ± 0.20 |
| isoxazole-3-carboxylic acid | 1.72 ± 0.42 |
| benzo[d]isoxazole-3-carboxylic acid | 2.09 ± 0.25 |

FIG. 4B – Table 2B

| Substrate Kinetic Parameters for Aspartate N-acetyltransferase | | | |
|---|---|---|---|
| Substrates | $k_{cat}$ (mU/mg) | K$_m$ (mM) | relative $k_{cat}/K_m$ (%) |
| Physiological substrates | | | |
| acetyl-CoA | | 0.0031 ± 0.0012 | |
| L-aspartate | 71 ± 6 | 0.16 ± 0.05 | 100 |
| Alternative substrates | | | |
| β-methylaspartate | 18 ± 2 | 0.36 ± 0.13 | 11.2 |
| 2,3-diaminosuccinate | 35 ± 5 | 0.92 ± 0.19 | 8.6 |
| L-glutamate | 23 ± 4 | 8.6 ± 1.6 | 0.59 |

FIG. 5

| Table 3: Dicarboxylic Acid Inhibitors of ANAT | |
|---|---|
| Inhibitors | $K_i$ (mM) |
| 2-bromofumaric acid | 0.37 ± 0.11 |
| 2-chlorofumaric acid | 0.41 ± 0.05 |
| 2,3-dibromosuccinic acid | 0.70 ± 0.08 |
| 2-bromosuccinic acid | 0.88 ± 0.13 |
| 2-methylsuccinic acid | 0.94 ± 0.17 |
| L-2-chlorosuccinic acid | 1.01 ± 0.13 |
| D-2-chlorosuccinic acid | 1.07 ± 0.14 |
| 2-methylfumaric acid | 1.34 ± 0.15 |
| trans-aconitic acid | 1.38 ± 0.20 |
| trans-epoxysuccinic acid | 1.41 ± 0.23 |
| 3-hydroxy-3-methylglutaric acid | 1.55 ± 0.14 |
| cis-aconitic acid | 1.73 ± 0.92 |
| 2-hydroxymalonic acid | 1.83 ± 0.55 |

FIG. 6 - Table 3

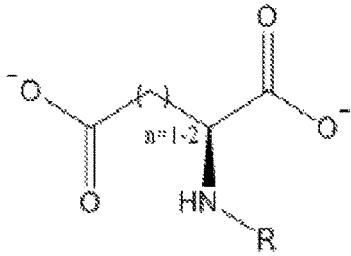

| Table 4: N-derivatized Amino Acid Inhibitors | | |
|---|---|---|
| R group | n | $K_i$ (mM) |
| 3-phenylpropanoyl | 1 | 0.032 ± 0.003 |
| 2-phenylethanoyl | 1 | 0.46 ± 0.08 |
| benzoyl | 1 | > 2 |
| benzoyl | 2 | 0.13 ± 0.01 |
| butyryl | 2 | 0.27 ± 0.02 |
| 3,5-(trifluoromethyl)benzoyl | 2 | 0.66 ± 0.05 |
| 4-(methylphenyl)sulfonyl | 1 | 1.25 ± 0.27 |
| cyclohexyl | 1 | 1.54 ± 0.38 |

FIG. 7 - Table 4

| [Asp-NH-(CH2)n-R structure] | [tBuO-] | [3,5-(CF3)2-C6H3-] | [cyclohexyl] | [Ph-] | [Ph-CH2-] | [Ph-(CH2)2-] | [Ph-CH2-O-] | [branched alkyl-Ph] |
|---|---|---|---|---|---|---|---|---|
| n = 0 | ... | >2 mM | ... | ... | ... | 14 mM | ... | ... |
| n = 1 | 280 µM | 660 µM | >2 mM | >2 mM | 455 µM | 31 µM | 17 µM | 197 µM |
| n = 2 | 764 µM | >2 mM | 572 µM | 130 µM | 248 µM | 39 µM | 12 µM | 608 µM |
| n = 3 | ... | ... | ... | 1.6 mM | 1.1 mM | 2.9 mM | 2.3 mM | 740 µM |

FIG. 8 – Table 5

FIG. 9 – Table 6

Table 7: N-Aryl aspartate derivatives as potential ANAT inhibitors

| No. | m | R | $K_i$ (mM) |
|---|---|---|---|
| 17 | 0 | benzyl | 1.23 ± 0.25 |
| 18 | 1 | ethylbenzyl | 0.49 ± 0.06 |
| 19 | 2 | propylbenzyl | 0.24 ± 0.04 |
| 20 | 3 | butylbenzyl | 0.19 ± 0.02 |

FIG. 10 - Table 7

Table 8: N-Alkyl substitutions on aspartate, glutamate and aminoadipate core structures

| No. | core | R | $K_i$ (mM) |
|---|---|---|---|
| 21 | aspartate derivatives (n = 1) | tert-butyl carbanoyl | |
| 22 | | 2-bromoacetyl | > 2 |
| 23 | | 2-chloroacetyl | 0.2 |
| 24 | glutamate derivatives (n = 2) | tert-butyl carbanoyl | 0.28 ± 0.01 |
| 25 | | butyryl | 0.27 ± 0.02 |
| 26 | | 4-butanoic-1-carbonyl | |
| 27 | | 3-propanoic-1-carbonyl | |
| 28 | 2-aminoadipate derivatives (n = 3) | tert-butyl carbanoyl | 0.76 ± 0.10 |
| 29 | | butyryl | > 2 |
| 30 | | 4-butanoic-1-carbonyl | >2 |
| 31 | | 3-propanoic-1-carbonyl | >2 |

FIG. 11 - Table 8

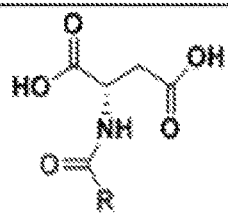
FIG. 12 - Table 9
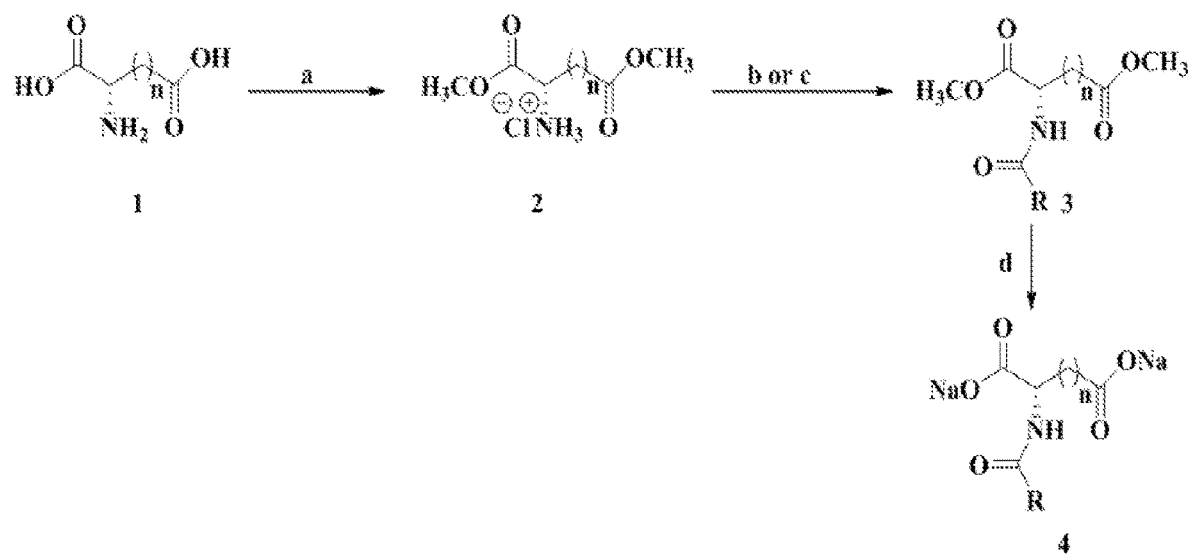
FIG. 13 - Scheme 1

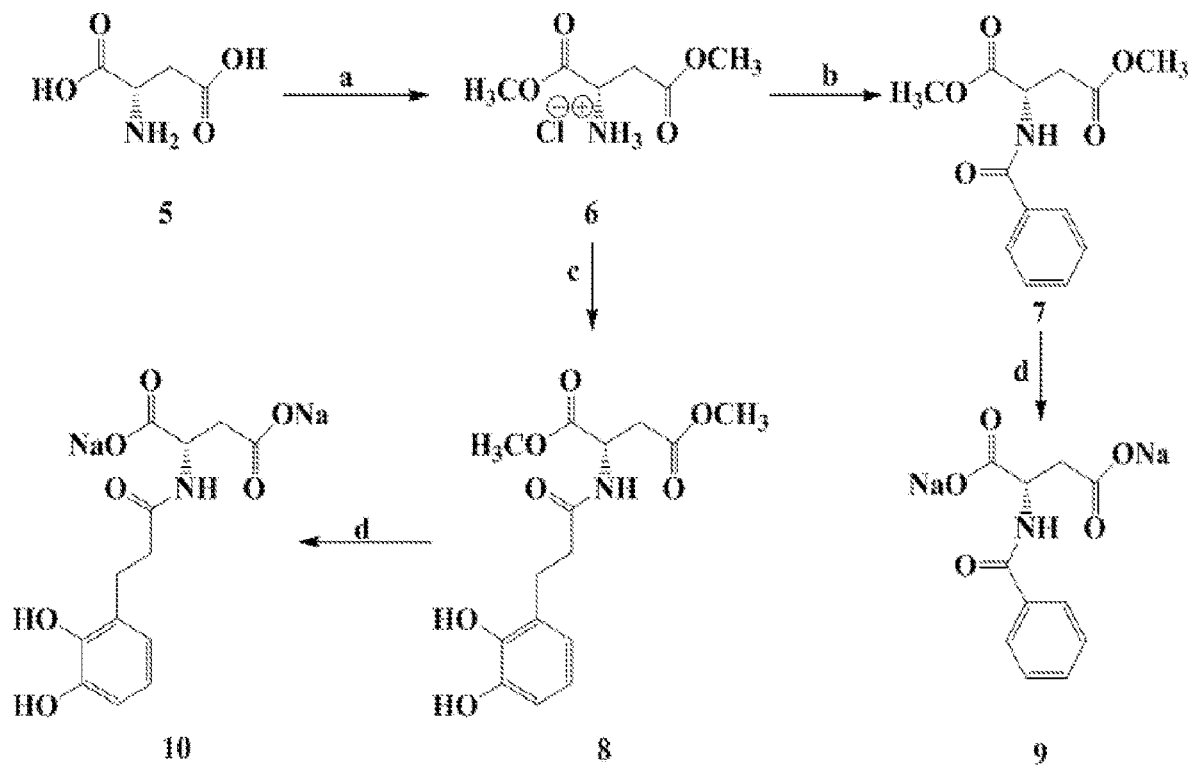
FIG. 14 - Scheme 2
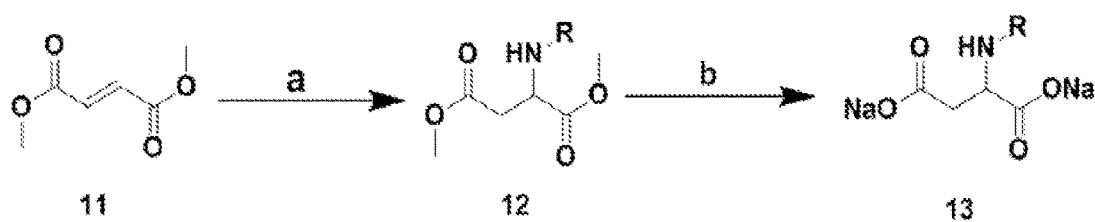
FIG. 15 - Scheme 3

POTENT INHIBITORS OF ASPARTATE N-ACETYL-TRANSFERASE FOR THE TREATMENT OF CANAVAN DISEASE

CROSS-REFERENCE TO RELATED APPLICATIONS

This application is a national stage application filed under 35 U.S.C. § 371 of international application PCT/US2017/023775, filed under the authority of the Patent Cooperation Treaty on Mar. 23, 2017, which claims priority to U.S. Provisional Application Ser. No. 62/313,902 filed under 35 U.S.C. § 111(b) on Mar. 28, 2016, the disclosure of which is incorporated herein by reference in its entirety.

STATEMENT REGARDING FEDERALLY SPONSORED RESEARCH

This invention was made with no government support. The government has no rights in this invention.

BACKGROUND OF THE INVENTION

Defects in the metabolism of N-acetyl-L-aspartate (NAA) have been shown to be the underlying cause of a fatal neurological disorder called Canavan disease (CD), for which there are currently no known effective treatments. While this is a rare disease, there is a critical need for treatment options.

Canavan disease is caused by mutations in the gene that codes for the enzyme aspartoacylase, the enzyme responsible for the deacetylation of NAA in the brain. As a consequence, NAA accumulates to high levels in patients with Canavan disease. NSA accumulation is known to be the critical factor for the development of Canavan disease symptoms. Multiple mutations in the acy2 gene that codes for aspartoacylase lead to mutant enzyme forms with inadequate catalytic potential to produce sufficient levels of acetate or to lower the accumulation of NAA that is the diagnostic hallmark of CD. For many years, the prevailing opinion had linked this acetate deficiency to the brain developmental disorders that are apparent in CD patients. However, it has been shown that a knockout of the Nat81 gene that codes for aspartate N-acetyltransferase (ANAT), the enzyme which catalyzes NAA synthesis, leads to a reversal of the CNS demyelination in an animal model of CD, but also appears to cause increased survival risks. It would therefore be advantageous to discover ANAT inhibitors usable to adjust brain NAA levels back into the physiological range and thereby treat the symptoms of CD without introducing increased risks.

SUMMARY OF THE INVENTION

Provided is a compound comprising Formula I or Formula II:

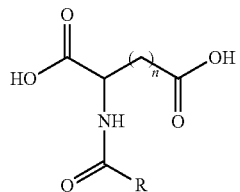

Formula I

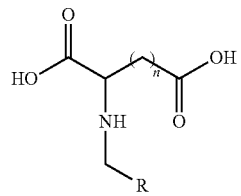

Formula II where n is either 0 or an integer from 1 to 3, and R is a substituted or unsubstituted aryl, aralkyl, alkoxy, or aryloxy. Also provided are salts, stereoisomers, prodrugs, racemates, solvates, hydrates, and polymorphs thereof.

In certain embodiments, the compound comprises Formula I, and n is 1 or 2. In certain embodiments, the compound comprises Formula II, and n is 1. In certain embodiments, R comprises a phenyl group. In certain embodiments, R comprises an ester. In particular embodiments, the ester is a butyl ester. In particular embodiments, the ester is a phenyl ester. In certain embodiments, R comprises a trifluoromethyl substituted phenyl. In certain embodiments, R comprises a tert-butyl substituted phenyl. In certain embodiments, R is 3,5-(trifluoromethyl)benzene. In certain embodiments, the R is selected from the group consisting of:

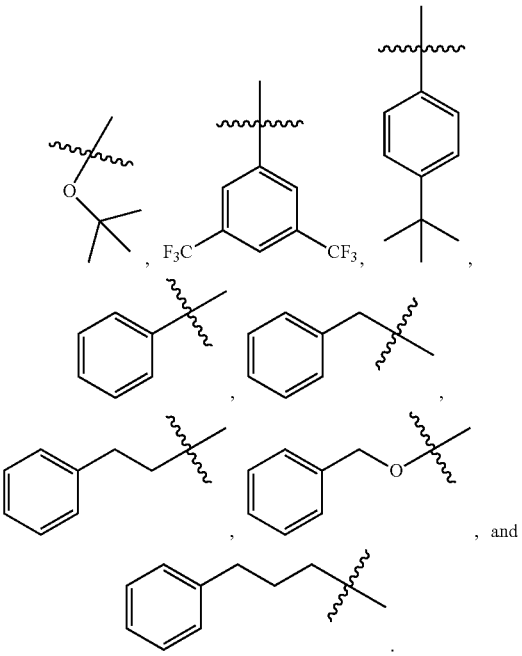

In certain embodiments, the compound comprises Formula I, R is

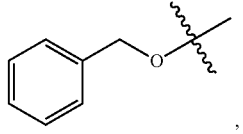

and n=1 or 2.

In certain embodiments, the compound comprises Formula I, R is

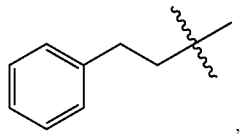

and n=1 or 2.

In certain embodiments, the compound comprises Formula II, R is

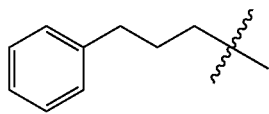

and n=1.

In certain embodiments, the compound is selected from the group consisting of: N-carbobenzyloxy-L-glutamic acid, N-(1-oxo-3-phenylpropyl)-L-aspartic acid, N-[(benzyloxy)carbonyl]-L-aspartic acid, N-chloroacetyl-L-aspartic acid, N-(t-butoxycarbonyl)-L-aspartic acid, N-[(4-methylphenyl)sulfonyL]-L-proline, N-methyl-DL-aspartic acid, N-alanyl-L-aspartic acid, 2-(3-chloro-6-oxopyridazin-1(6H)-yl)acetic acid, isoxazole-3-carboxylic acid, and benzo[d]isoxazole-3-carboxylic acid.

In certain embodiments, the compound has Formula IF1:

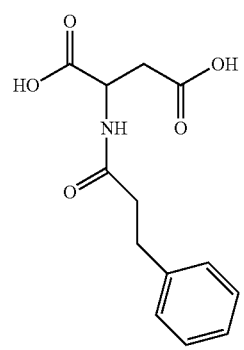

Formula IF1

In certain embodiments, the compound has Formula IF2:

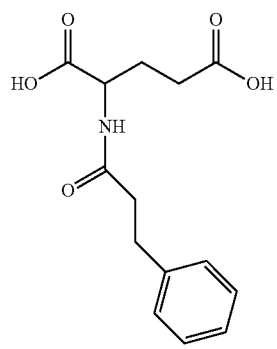

Formula IF2

In certain embodiments, the compound has Formula IG1:

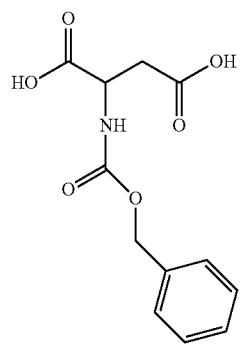

Formula IG1

In certain embodiments, the compound has Formula IG2:

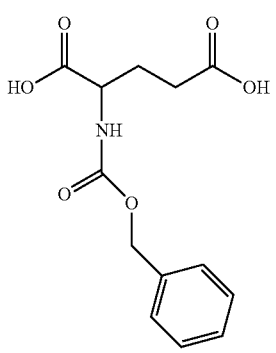

Formula IG2

In certain embodiments, the compound has Formula IIH1:

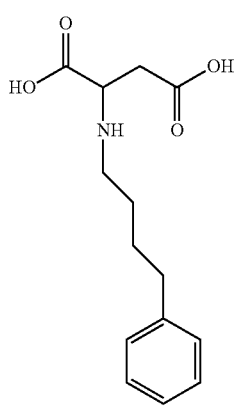

Formula IIH1

Also provided is a pharmaceutical composition comprising an effective amount of a compound of Formula I or Formula II; and a pharmaceutically acceptable carrier, diluent, or adjuvant.

Also provided is a method of making a compound herein, the method comprising reacting a hydrochloride dimethylester with either a halide or an acid to produce an N-acyl derivative dimethylester; and hydrolyzing the N-acyl derivative dimethylester to produce a compound of Formula I or Formula II. In certain embodiments, the hydrochloride dimethylester is produced by reacting thionyl chloride with one of aminomalonate, aminoaspartate, amino glutamate, or 2-aminoadipate.

Also provided is a method of making a compound herein, the method comprising reacting dimethyl fumarate with an amine hydrochloride in the presence of a base to produce an N-alkyl-DL-aspartic acid dimethylester; and hydrolyzing the N-alkyl-DL-aspartic acid dimethylester to produce a compound of Formula I or Formula II.

Also provided is a method of treating, preventing, or ameliorating Canavan disease, the method comprising administering an effective amount of a compound of Formula I or Formula II to a subject in need thereof, and treating, preventing, or ameliorating Canavan disease in the subject. In certain embodiments, the subject is a human.

Also provided is a method of inhibiting ANAT activity in a cell, the method comprising administering an effective amount of a compound of Formula I or Formula II to a cell, and inhibiting ANAT activity in the cell. In certain embodiments, the cell is a brain cell. In certain embodiments, the cell is in a human subject.

Also provided is a kit for making an ANAT inhibitor compound, the kit comprising a first container housing an N-acyl dimethylester, and a second container housing a halide or an acid. Also provided is a kit for making an ANAT inhibitor compound, the kit comprising a first container housing an amine hydrochloride, and a second container housing a dimethyl fumarate.

BRIEF DESCRIPTION OF THE DRAWINGS

The patent or application file contains one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 2: Table 1, showing a summary of a compound library screening against ANAT.

FIG. 3: Dioic acid core structure. The N-acylated side chain is shown in red.

FIG. 4A: Table 2, showing N-acylation derivatives of aminomalonic, aspartic, glutamic, and aminoadipic acids. *Substitutions shown in red indicate the best inhibitors in the compound class.

FIG. 4B: Table 2B, displaying certain substrate analog inhibitors of ANAT in order from most potent (top) to least potent (bottom).

FIG. 5: Substrate kinetic parameters for aspartate N-acetyltransferase. The enzyme is quite selective for aspartic acid as the acetyl group acceptor.

FIG. 6: Table 3, showing dicarboxylic acid inhibitors of ANAT.

FIG. 7: Table 4, showing N-derivatized amino acid inhibitors of ANAT.

FIG. 8: Table 5, showing N-acyl amino acid derivatives.

FIG. 9: Table 6, showing N-aroyl amino acid derivatives.

FIG. 10: Table 7, showing N-aryl aspartate derivatives as ANAT inhibitors.

FIG. 11: Table 8, showing N-alkyl substitutions on aspartate, glutamate, and aminoadipate core structures.

FIG. 12: Table 9, showing the substituent effects in N-acyl aspartic acid derivatives.

FIG. 13: Scheme 1, showing the general synthetic scheme for the preparation of N-acylated amino acids.

FIG. 14: Scheme 2, showing the synthetic scheme for the preparation of sodium N-benzoyl-L-aspartate (9) and sodium N-(3-(2,3-dihydroxyphenyl)propanoyl)-L-aspartate (10). Reagents and conditions: (a) $SOCl_2$ in MeOH at 0° C. to RT 14 h; (b) benzoyl chloride, $NaHCO_3$ in DCM and $H_2O$, RT, 8 h; (c) 3-phenylpropanoic acid, EDCl, $Et_3N$ in DCM, 0° C. to RT, 3 h; (d) NaOH in THF and $H_2O$, RT, 5 h.

FIG. 15: Scheme 3, showing the synthesis of N-alkyl-DL-aspartate derivatives. Reagents and conditions: (a) pyridine, amine hydrochloride, triethylamine 100° C., 5 h; (b) 1 N NaOH, r.t., 3 h.

DETAILED DESCRIPTION OF THE INVENTION

Figure 1:
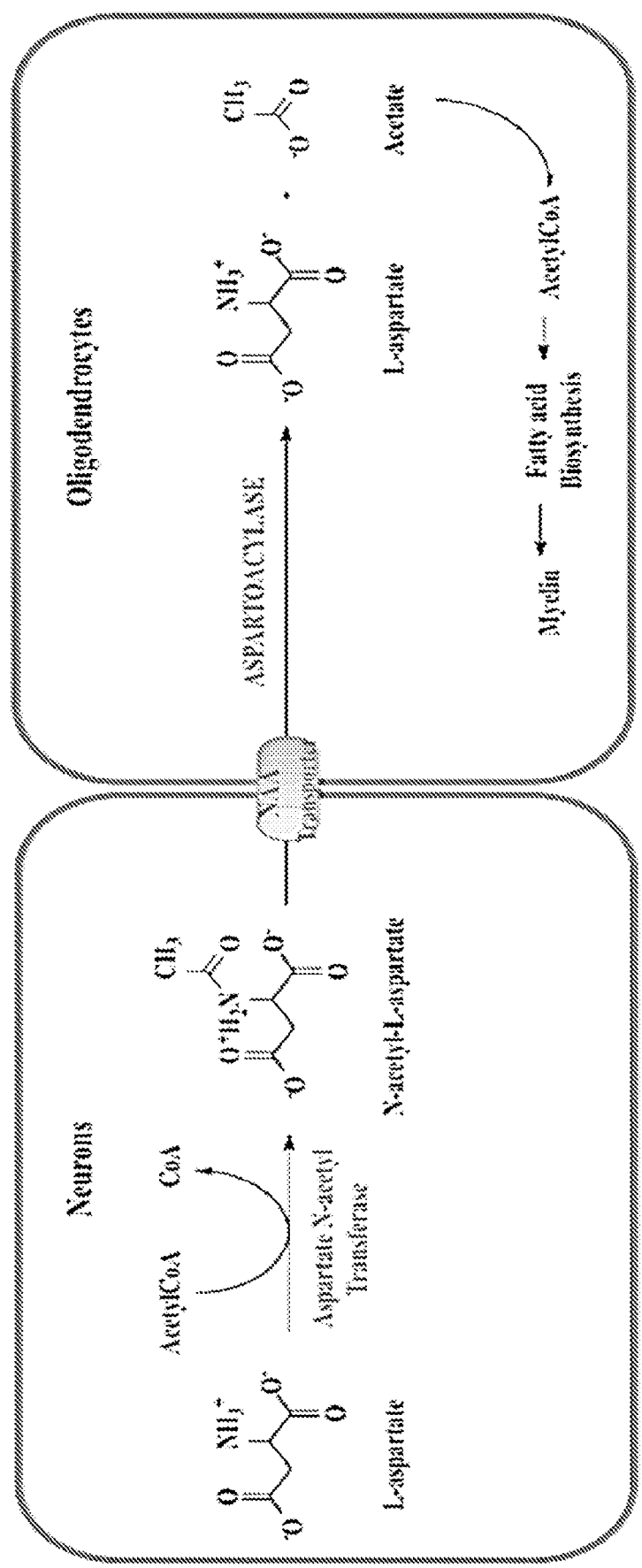
FIG. 1: Scheme showing the transfer of an acetyl group to L-aspartate acid to produce NAA in the brain, catalyzed by the enzyme aspartate N-acetyltransferase (ANAT).

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

For convenience, various terms are defined prior to further description of the various embodiments of the present disclosure.

It will be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

It will also be appreciated by one of ordinary skill in the art that asymmetric centers may exist in any of the compounds disclosed herein. Thus, the compounds and pharmaceutical compositions thereof may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs."

The term "hydrate" refers to a solvate with water.

The term "racemate" refers to a mixture that contains an equal amount of enantiomers.

The term "polymorph" means a crystalline form of a substance that is distinct from another crystalline form of the substance but that shares the same chemical formula.

The term "prodrug" refers to a precursor or derivative of a particular compound which, when consumed, generates the pharmacologically active compound by action of natural processes or biological conditions. For example, a prodrug can be cleaved, hydrolyzed, or oxidized by enzymes in vivo to produce the pharmacologically active compound.

The term "alkyl" means a functional group or substituent derived from an alkane missing one hydrogen. "Alkyl" can be a straight or branched alkyl such as, but not limited to, methyl, ethyl, propyl, tert-butyl, or sec-butyl. The number of carbons in alkyl may be specified. For example, "$C_1$-$C_6$ alkyl" means an alkyl as described above containing from 1 to 6 carbon atoms.

The term "haloalkyl" means an alkyl as described above wherein one or more hydrogens are replaced by halo. The term "halo" means fluoro, chloro, bromo, or iodo.

The term "aryl" refers to a functional group containing, or derived from, an aromatic ring. Aryl groups include, but are not limited to, phenyl, naphthyl, thienyl, indolyl, or any of the preceding functional groups substituted by $C_1$-$C_6$ alkyl, one or more halogens, trifluoromethyl, or lower alkyl or lower alkoxy moieties.

The term "acyl" refers to a functional group derived from an oxoacid having one or more hydroxyl groups removed. An acyl group contains a double bonded oxygen atom and an alkyl group. The number of carbons in acyl may be specified. For example, "$C_n$-acyl" refers to a radical having a single carbon atom of a carbonyl group as the point of attachment, further having a linear or branched, cyclic or acyclic structure, further having a total of n carbons, 1 or more hydrogen atoms, and a total of one oxygen atom.

The term "aryloxy" means an aryl group singular bonded to oxygen. A non-limiting example of an aryloxy group is phenoxy, $C_6H_5O$—.

The term "alkoxy" means an alkyl group singular bonded to oxygen.

The term "aralkyl" refers to a radical derived from an alkyl radical by replacing one or more hydrogen atoms with one or more aryl groups. In other words, an aralkyl group is an aryl-substituted alkyl group.

The term "pharmaceutically acceptable salts," as used herein, refers to salts of compounds of the present disclosure that are substantially non-toxic to living organisms. Typical pharmaceutically acceptable salts include those salts prepared by reaction of a compound of the present disclosure with an inorganic or organic acid, or an organic base, depending on the substituents present on the compounds.

Examples of inorganic acids which may be used to prepare pharmaceutically acceptable salts include: hydrochloric acid, phosphoric acid, sulfuric acid, hydrobromic acid, hydroiodic acid, phosphorous acid, and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids, and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts are known to one of ordinary skill in the art.

Suitable pharmaceutically acceptable salts may also be formed by reacting the compounds of the present disclosure with an organic base such as methylamine, ethylamine, ethanolamine, lysine, ornithine, and the like. Other suitable salts are known to one of ordinary skill in the art.

It should be recognized that the particular anion or cation forming a part of any salt is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use—A Handbook, by C. G. Wermuth and P. H. Stahl, Verlag Helvetica Chimica Acta, 2002, which is incorporated herein by reference.

GENERAL DESCRIPTION

Provided are N-derivatives of amino acids that are potent inhibitors of aspartate N-acetyltransferase (ANAT), which is the brain enzyme responsible for the synthesis of N-acetyl-L-aspartate (NAA). ANAT catalyzes the transfer of an acetyl group to L-aspartate acid to produce NAA in the brain. (FIG. 1.) The accumulation of NAA has been shown to be the causative agent of Canavan disease, a rare developmental brain disorder. Elevated NAA is one of the underlying causes of Canavan disease. Therefore, inhibition of ANAT can be a treatment option for the currently untreatable Canavan disease by lowering NAA levels in patients with the disease. The inhibitors described herein can lower elevated levels of NAA and thereby serve as a treatment for Canavan disease.

In general, the the ANAT inhibitor compounds herein are dioic acids having the formula of Formula A:

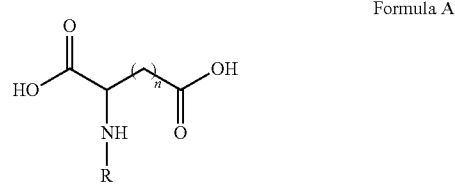

Formula A where n is from 0 to 3, and R is a substituted or unsubstituted acyl, aryl, aralkyl, alkoxy, or aryloxy.

The compounds of Formula A include two classes of compounds: those having an acyl group and those without an acyl group. Thus, more specifically, the ANAT inhibit compounds herein have either Formula I or Formula II:

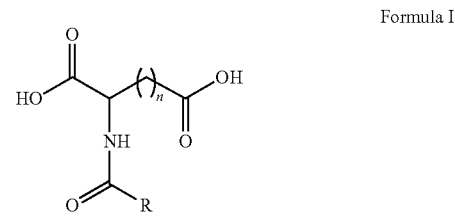

Formula I

-continued

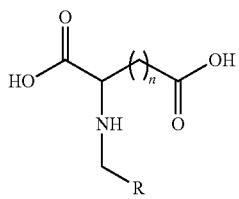

Formula II where n ranges from 0 to 3, and R is a substituted or unsubstituted aryl, aralkyl, alkoxy, or aryloxy. When n is 0, the compound is an aminomalonate derivative. When n is 1, the compound is an L-aspartic acid derivative. When n is 2, the compound is a L-glutamic acid derivative. When n is 3, the compound is a 2-aminoadipic acid derivative. Especially suitable R groups for Formula I or Formula II include, but are not limited to, the following:

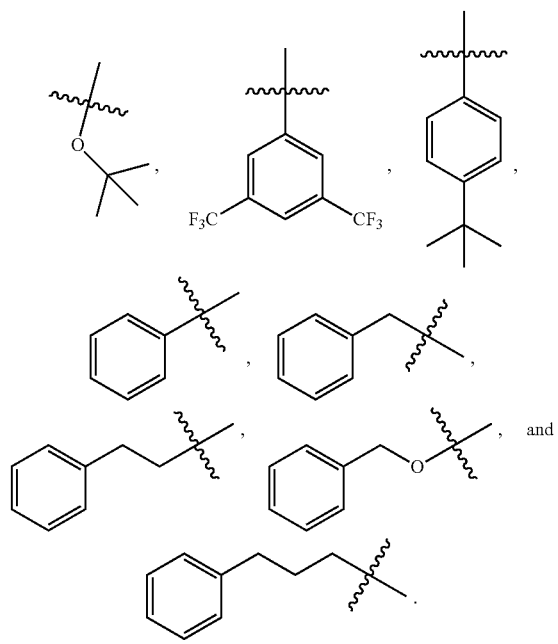

In some embodiments, the R group of Formula I or Formula II is substituted, such as with one or more halogens, or with one or more $C_1$-$C_6$ alkyl groups.

In one non-limiting example, the ANAT inhibitor compound has the following structural formula, referred to as Formula IA1:

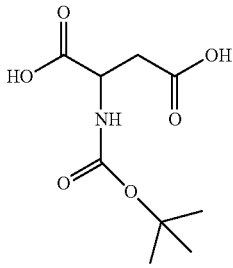

Formula IA1

In one non-limiting example, the ANAT inhibitor compound has the following structural formula, referred to as Formula IA2:

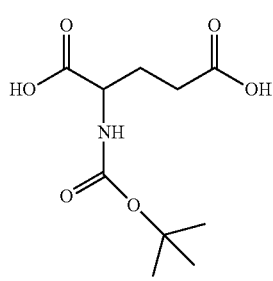

Formula IA2

In one non-limiting example, the ANAT inhibitor compound has the following structural formula, referred to as Formula IA3:

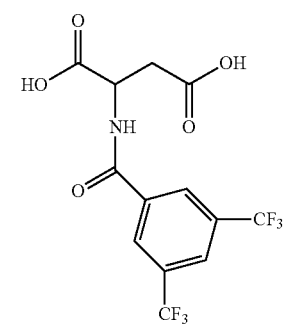

Formula IA3

In one non-limiting example, the ANAT inhibitor compound has the following structural formula, referred to as Formula IB1:

Formula IB1

In one non-limiting example, the ANAT inhibitor compound has the following structural formula, referred to as Formula IB2:

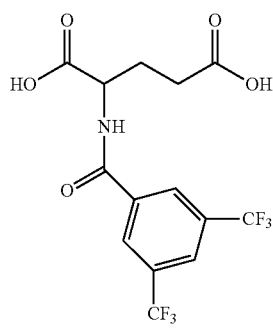

Formula IB2

In one non-limiting example, the ANAT inhibitor compound has the following structural formula, referred to as Formula IB3:

Formula IB3

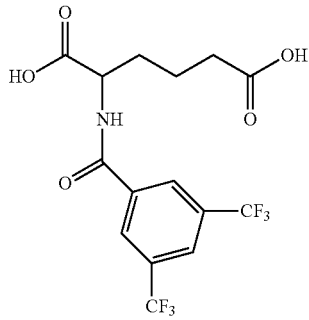

In one non-limiting example, the ANAT inhibitor compound has the following structural formula, referred to as Formula IC1:

Formula IC1

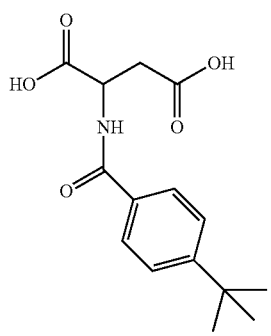

In one non-limiting example, the ANAT inhibitor compound has the following structural formula, referred to as Formula IC2:

Formula IC2

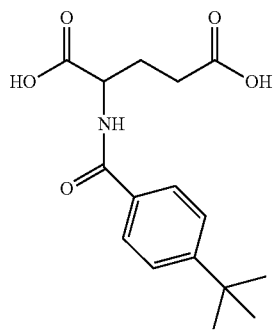

In one non-limiting example, the ANAT inhibitor compound has the following structural formula, referred to as Formula IC3:

Formula IC3

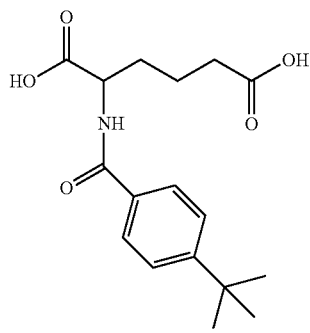

In one non-limiting example, the ANAT inhibitor compound has the following structural formula, referred to as Formula ID1:

Formula ID1

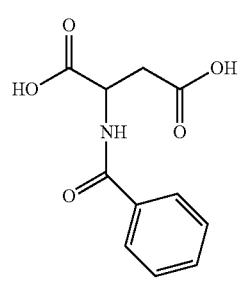

In one non-limiting example, the ANAT inhibitor compound has the following structural formula, referred to as Formula ID2:

Formula ID2

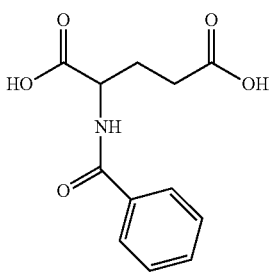

In one non-limiting example, the ANAT inhibitor compound has the following structural formula, referred to as Formula ID3:

Formula ID3

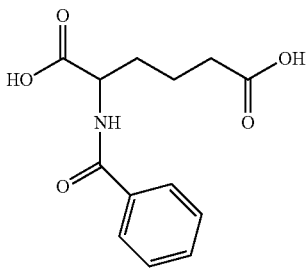

In one non-limiting example, the ANAT inhibitor compound has the following structural formula, referred to as Formula IE1:

Formula IE1

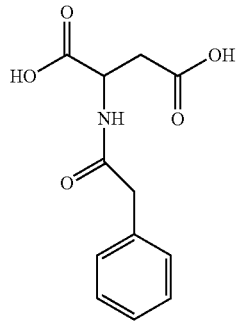

In one non-limiting example, the ANAT inhibitor compound has the following structural formula, referred to as Formula IE2:

Formula IE2

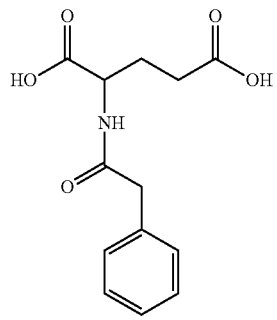

In one non-limiting example, the ANAT inhibitor compound has the following structural formula, referred to as Formula IE3:

Formula IE3

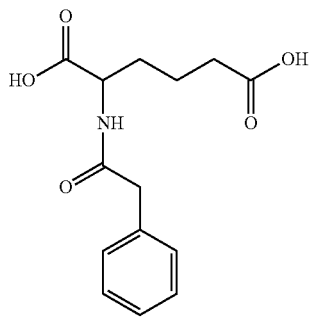

In one non-limiting example, the ANAT inhibitor compound has the following structural formula, referred to as Formula IF1 (also referred to herein as compound 4):

Formula IF1

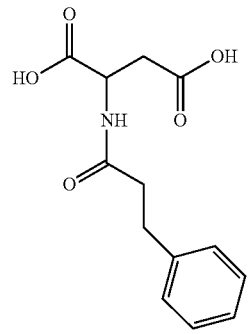

In one non-limiting example, the ANAT inhibitor compound has the following structural formula, referred to as Formula IF2:

Formula IF2

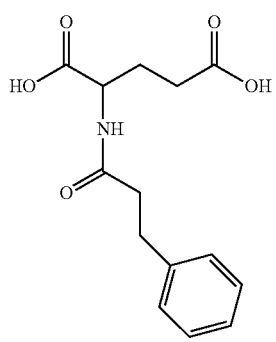

In one non-limiting example, the ANAT inhibitor compound has the following structural formula, referred to as Formula IF3:

Formula IF3

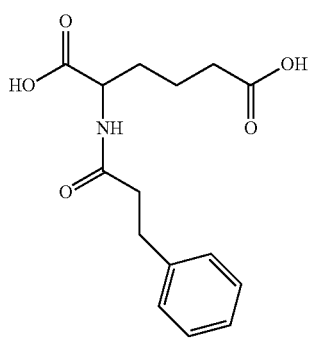

In one non-limiting example, the ANAT inhibitor compound has the following structural formula, referred to as Formula IG1 (also referred to herein as compound 5):

Formula IG1

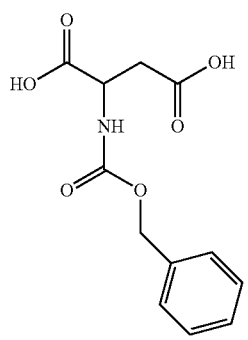

Formula IH1

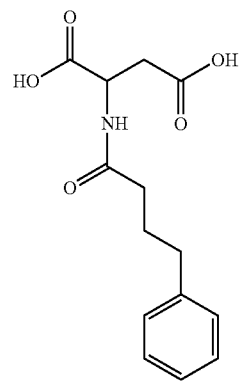

In one non-limiting example, the ANAT inhibitor compound has the following structural formula, referred to as Formula IG2:

In one non-limiting example, the ANAT inhibitor compound has the following structural formula, referred to as Formula IH2:

Formula IG2

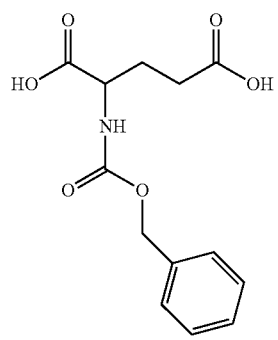

Formula IH2

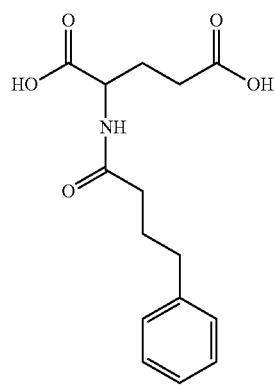

In one non-limiting example, the ANAT inhibitor compound has the following structural formula, referred to as Formula IG3:

In one non-limiting example, the ANAT inhibitor compound has the following structural formula, referred to as Formula IH3:

Formula IG3

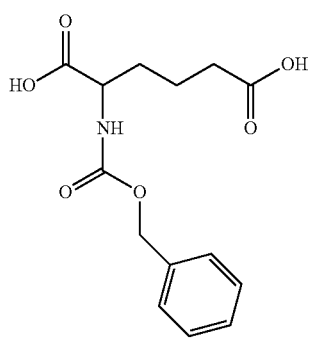

Formula IH3

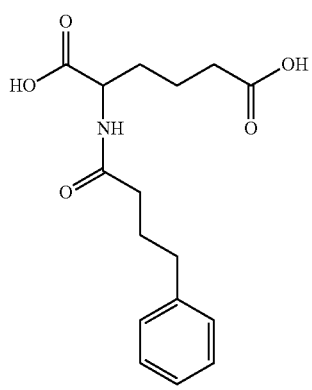

In one non-limiting example, the ANAT inhibitor compound has the following structural formula, referred to as Formula IH1:

In one non-limiting example, the ANAT inhibitor compound has the following structural formula, referred to as Formula IF0:

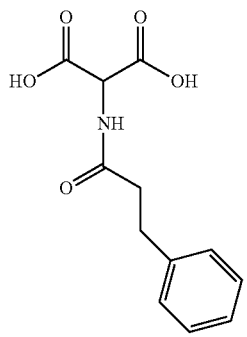

Formula IF0

In one non-limiting example, the ANAT inhibitor compound has the following structural formula, referred to as Formula IIA1:

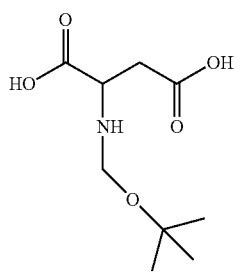

Formula IIA1

In one non-limiting example, the ANAT inhibitor compound has the following structural formula, referred to as Formula IIB1:

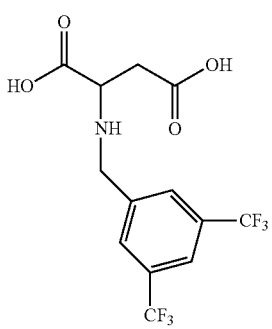

Formula IIB1

In one non-limiting example, the ANAT inhibitor compound has the following structural formula, referred to as Formula IIC1:

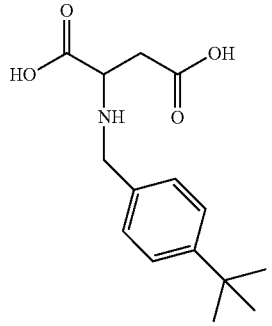

Formula IIC1

In one non-limiting example, the ANAT inhibitor compound has the following structural formula, referred to as Formula IID1:

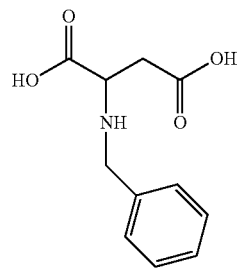

Formula IID1

In one non-limiting example, the ANAT inhibitor compound has the following structural formula, referred to as Formula IIE1:

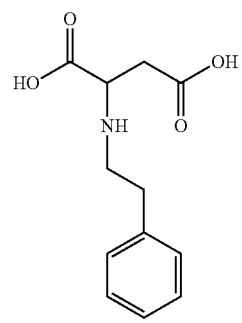

Formula IIE1

In one non-limiting example, the ANAT inhibitor compound has the following structural formula, referred to as Formula IIF1:

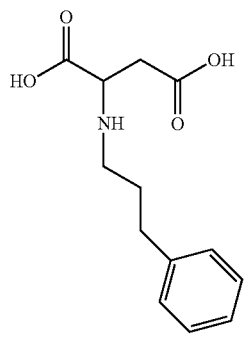

Formula IIF1

In one non-limiting example, the ANAT inhibitor compound has the following structural formula, referred to as Formula IIG1:

Formula IIG1

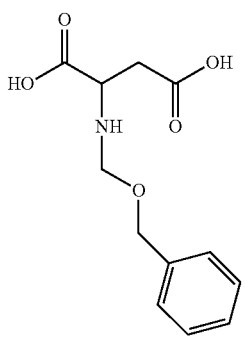

In one non-limiting example, the ANAT inhibitor compound has the following structural formula, referred to as Formula IIH1:

Formula IIH1

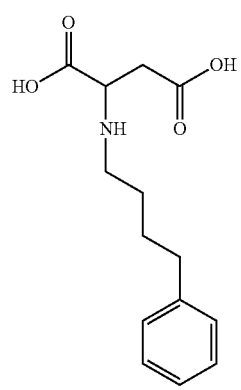

The compounds of Formula I can be synthesized through a variety of methods, such as those illustrated in Schemes 1-2 (FIGS. 13-14). The starting material is generally aminomalonate, aspartate, glutamate, or 2-aminoadipate, the selection of which determines the value of n in the resulting compound of Formula I. In some embodiments, the aminomalonate, aspartate, glutamate, or 2-aminoadipate is dissolved in a suitable solvent (such as methanol) and reacted with thionyl chloride to obtain a hydrochloride dimethylester. The hydrochloride dimethylester is then reacted with either (i) an R group halide, or (ii) an R group acid in the presence of a suitable base (such as triethylamine), to produce an N-acyl derivative having the R group. In one non-limiting example, starting from aminoaspartate, the R group halide is benzoyl chloride, resulting in a dimethyl benzoyl-L-aspartate derivative. In another non-limiting example, starting from aminoaspartate, the R group acid is 3-phenylpropanoic acid, resulting in a dihydroxyphenylpropanoyl-L-aspartate derivative. The methyl esters of the N-acyl derivative are then hydrolyzed to produce a salt of the N-acyl derivative having the R group. The skilled practitioner will recognize that many other synthetic approaches for preparing the compounds of Formula I are possible and encompassed within the present disclosure.

Similarly, the compounds of Formula II can be synthesized through a variety of methods, such as the method illustrated in Scheme 3 (FIG. 15). In some embodiments, dimethyl fumarate is reacted with an amine hydrochloride in the presence of a suitable base (such as triethylamine) to produce an N-alkyl-DL-aspartic acid dimethylester. The methyl esters are then hydrolyzed to produce a salt of the N-derivatized-DL-aspartic acid. The skilled practitioner will recognize that many other synthetic approaches for preparing the compounds of Formula II are possible and encompassed within the present disclosure.

Identifying and developing effective enzyme inhibitors requires the availability of a selective enzyme activity assay and the isolation and purification of the target enzyme. A fixed-time ANAT assay using radiolabeled NAA has been developed, but the membrane-associated nature of ANAT makes enzyme purification a significant challenge. ANAT is difficult to purify. However, in order to test the ANAT inhibitory activity of any compounds, a stable, soluble, and active form of the enzyme ANAT has to be produced. This can be accomplished, for example, as described in U.S. Provisional Patent Application No. 62/216,700, which is incorporated herein by reference for all purposes. Briefly, fusion enzyme constructs can be used to successfully solubilize and purify ANAT as a maltose binding protein (MBP) fusion. This MBP-ANAT fusion construct is stable, soluble, and highly active, and is suitable for scaled-up production and high-throughput screening studies. An optimized thiol detection assay can be used to kinetically characterize this newly produced enzyme form. The ANAT inhibitor compounds described herein were screened to yield selective, low micromolar inhibitors of this key regulator of brain NAA metabolism using such methods. As described in the Examples, the compounds of Formula I and Formula II are potent ANAT inhibitors.

Pharmaceutical compositions of the present disclosure comprise an effective amount of a compound of Formula I or Formula II (an "active" ingredient), and/or additional agents, dissolved or dispersed in a pharmaceutically acceptable carrier. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid, or aerosol form, and whether it needs to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active ingredient. In other embodiments, an active ingredient may comprise between about 2% to about 75% of the weight of the unit, or between about 25% to about 60%, for example, and any range derivable therein. Naturally, the amount of active ingredient(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543, 158; 5,641,515, and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In particular embodiments, the compounds and compositions described herein are useful for treating, preventing, or ameliorating Canavan disease. Furthermore, the compounds and compositions herein can be used in combination therapies. That is, the compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active ingredient in a way that the therapeutic effects of the first administered procedure or drug is not entirely disappeared when the subsequent procedure or drug is administered.

It is further envisioned that the compositions and methods described herein can be embodied in the form of a kit or kits.

A non-limiting example of such a kit is a kit for making an ANAT inhibitor compound, the kit comprising an N-acyl dimethylester and either a halide or an acid in separate containers, where the containers may or may not be present in a combined configuration. Alternatively, a kit can comprise dimethyl fumarate and an amine hydrochloride in separate containers, where the containers may or may not be present in a combined configuration. Many other kits are possible, such as kits for making a pharmaceutical composition that further comprise a pharmaceutically acceptable carrier, diluent, or excipient. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Further provided is a method of determining coverage of health insurance reimbursement or payments, the method comprising denying coverage or reimbursement for a treatment, wherein the treatment comprises an ANAT inhibitor compound of Formula I or Formula II.

EXAMPLES

Initial Screening

A set of focused compound libraries was screened for ANAT inhibitors. The initial libraries were composed of amino acids, amino acid derivatives, various metabolites, and metabolite analogs. Examination of 256 initial compounds yielded a total of 17 moderate inhibitors that showed at least 50% inhibition of ANAT when examined at a concentration of 2 mM (Table 1, FIG. 2). The concentration of each inhibitor was varied in order to determine their affinity (K value) against ANAT. The most potent inhibitor from these libraries, an N-chloroacetyl derivative of the substrate, yielded a value of 200 μM. Next, a group of constrained amino acid analogs were examined, producing an additional set of moderate inhibitors, but one compound, the N-carbobenzyloxy derivative of L-aspartate—that is, N-[(benzyloxy)carbonyl]-L-aspartic acid—gave an unexpectedly potent value of 17 μM (Table 1, FIG. 2).

From this library screening, 21 unique compounds (plus 1 duplicate) showed significant inhibition of ANAT when examined at 2 mM (~6% hit rate). A total of 38 compounds were rejected due to high background signals (11% rejection rate). The values for the most potent of the substrate analog inhibitors are given in Table 2 (FIG. 4A), as well as in Table 2B (FIG. 4B) where the compounds are listed from most potent to least potent.

Four of the compounds that showed inhibition in the initial screening (Table 1, FIG. 2) were subsequently found to have values greater than 2 mM. These compounds (2-D-pyroglutamic acid, 3-(2-fluoro-phenyl)-isoxazole-5-carboxylic acid, 3-(3-methyl-1,2,4-oxadiazol-5-yl-benzoic acid, and methyl 2-oxo-1-pyrrolidineacetic acid) are not included in Table 2 or Table 2B.

An examination of the structures of these initial ANAT inhibitors, and the structures of screened compounds that did not inhibit this enzyme, reveals some structural features that appear to be important for good binding affinity. Substrate analogs containing an unmodified α-carboxylate group were found to be an important binding component, with modifications of this functional group resulting in impaired binding. For example, L-aspartic acid amide and L-aspartic acid α-esters are neither alternative substrates nor inhibitors of ANAT. However, changes at the α-amino position are well tolerated, with a number of N-derivatized aspartic acids found to function as ANAT inhibitors. (FIGS. 4A, 7-9.) In particular, an N-derivatized L-aspartic acid with a functional group containing an amide bond linkage to an aromatic ring, N-[(benzyloxy)carbonyl]-L-aspartic acid, shows surprisingly high potency (Table 2). Thus, without wishing to be bound by theory, it is believed that while changes at the α-carboxyl group are not well tolerated, even fairly extensive modifications to the α-amino are not only tolerated but can result in significantly improved binding affinity.

Screening of the metabolite library (Table 1, FIG. 2) produced an unexpectedly high hit rate (16%), calculated after eliminating 14 compounds that were not initially tested because of high background signals. This compound library contained an unusually high number of dicarboxylic acids, and each of the 13 ANAT inhibitors from this library were found to be dicarboxylic acids (Table 3, FIG. 6). While none of the dicarboxylic acids in Table 3 are particularly potent inhibitors of ANAT, this data indicates that the presence of appropriately positioned carboxylate functional groups provides reasonable binding affinity to the target enzyme. The range of derivatives that are tolerated at the interior carbons of these inhibitors (Table 3, FIG. 6) is consistent with the observation noted above that significant functional diversity is allowed at the α-carbon of the amino acid derivatives.

Aspartate Analog Derivative Inhibitors

Given the above screening results, a series of substrate analog derivatives were constructed to probe the substrate binding pocket of ANAT. Several different N-derivatized aspartic and glutamic acid analogs were synthesized to examine the binding potency that can be conferred through modifications at the α-amino position. Table 4 (FIG. 7) summarizes the structures of these N-derivatived amino acid inhibitors.

This set of synthesized derivatives shows that the enzyme is capable of binding both N-derivatized aspartate and glutamate analogs with reasonably high affinities. However, when comparing compounds with the same amine-functionalization, there is a clear binding preference for the longer glutamate structure. For example, N-benzoyl-L-glutamate is a 0.13 mM inhibitor, while the comparable L-aspartate derivative has a value greater than 2 mM (Table 4, FIG. 7). There is also a clear preference for N-aroyl derivatives over N-acyl derivatives. The most potent, low micromolar inhibitors each have a phenylethyl group attached either through an amide bond (Table 2, FIG. 4A) or a carbamoyl bond (Table 4, FIG. 7) to L-aspartic acid.

SAR Analysis

The structures of the best initial inhibitors that were identified by library screening against ANAT are reported in Table 1 (FIG. 2), along with a summary of the overall results from compound library screening. The structures of the most potent inhibitors provide information for optimal synthetic routes that can be pursued to develop improved binding affinity. These approaches include the modification of dioic acids, including L-aspartic acid, L-glutamic acid, and L-2-amino adipic acid, through the incorporation of a series of N-alkyl and N-aroyl substituents coupled by amide, carbamoyl, or N-sulfonyl linkages. The kinetic evaluation of these compounds (FIG. 5.) has established the optimal requirements needed in each structural quadrant for potent binding into the acetyl group acceptor site of ANAT.

Dioic Acid Inhibitor Optimization

Figure 9:
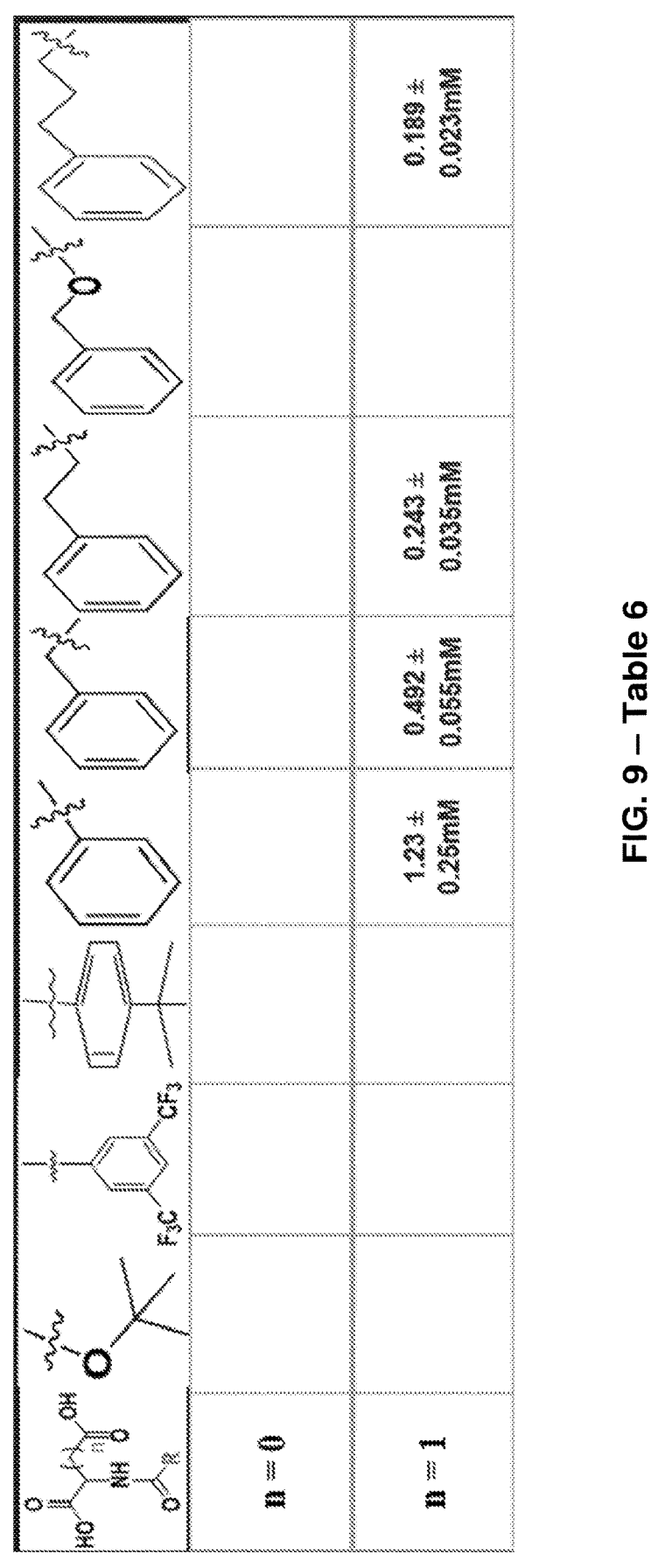

Given the observed requirement for properly positioned dicarboxylate groups, and the enhancement of ANAT inhibitor binding affinity through selective N-derivatization, a series of L-aspartate and L-glutamate derivatives were synthesized and tested. These compounds included both N-acyl derivatives (FIG. 8, Table 5) and N-aroyl derivatives (FIG. 9, Table 6).

The core dioic acid structure (FIG. 3) was systematically modified to determine the geometric properties that would lead to optimal inhibitor binding. During this process, a 2-amino dioic acid was considered the parent structure, with the chain length starting from L-aspartic acid (n=1), increasing to L-glutamic acid (n=2), and finally to 2-aminoadipic acid (n=3). Systematic variation of the chain length of the dioic acids, from n=0 (2-aminomalonic acid) to n=3 (2-aminoadipic acid), showed improved binding affinity for the L-aspartate (n=1) and L-glutamate (n=2) derivatives (FIG. 8, Table 5; FIG. 4A, Table 2).

Next, the nature of the N-acyl substituent was varied. To avoid any change in the stereochemistry, only the L-isomers of the dioic acids were used for derivatization. The length of the N-acylated side chain (indicated in red in FIG. 3) on these dioic acid core structures was varied from m=0 to 3, as well as the nature of the linker between the amino group and the acyl side chain (Table 2, FIG. 4A). Each of these compounds was synthesized as described below and then kinetically evaluated as potential inhibitors against ANAT. The determined inhibition constants (IQ show a systematic variation with the change in the values of n and m (Table 2, FIG. 4A). The optimal inhibitors obtained were from the phenylpropyl and the carbobenzyloxy derivatives of L-aspartate and L-glutamate (FIG. 8, Table 5, red box). To test the importance of the N-acyl linkage, a set of comparable N-aroyl derivatives was prepared. Howevever, in each case, these compounds were less potent inhibitors of ANAT (FIG. 9, Table 6).

The kinetic evaluation of this series of N-acyl dioic acid compounds against ANAT indicates that a value for n of 1 to 2 (aspartate or glutamate) and a value for m of 2, with either an acyl or an ester linkage, makes the optimal fit. A shorter dioic acid, aminomalonate, was also examined with the more potent phenylpropanoyl side chain, but was found to be a much less effective inhibitor than the longer dioic acids (Table 2, FIG. 4A).

Once the geometric constraints of the ANAT inhibitor binding site were systematically explored by varying the length of the dioic acid structure and the length of the N-linked side chain, the nature of the N-linkage, the requirement for an aryl vs. alkyl side chain, and the effect of aryl substituents were explored.

Evaluation of the Amide Linkage in the Optimized Core Structure

To determine if the amide linkage plays an important role in the binding of the dioic acid inhibitors, a series of structurally related N-aryl derivatives of L-aspartate were prepared and tested as inhibitors of ANAT. While each of the N-aryl derivatives are inhibitors of ANAT (Table 7, FIG. 4), these compounds have only moderate affinities, and the best inhibitors of this series (compounds 19 and 20) are significantly weaker inhibitors than the corresponding N-acyl and N-ester linked compounds (compounds 4 and 5) (Table 2, FIG. 4A).

Evaluation of the Aromatic Ring in the Side Chain

To determine if the aryl side chain plays a significant role in the binding affinity of the dioic acid inhibitors, a series of different N-alkyl derivatives of L-aspartate, L-glutamate, and L-aminoadipate were prepared and tested. Several of these N-alkyl compounds did not show any inhibition against ANAT when tested at 2 mM, while some were found to be moderate inhibitors (Table 8, FIG. 11). However, the best of these N-alkyl derivatives had $K_i$ values that are only in the several hundred micromolar range, which is significantly weaker than the related derivatives with N-acyl side chains on the same dioic acid structures.

Evaluation of the Effect of Substitutions on the Aryl Ring

Given the observed importance of the N-aryl side chain, a series of substituents were introduced into the aromatic ring to determine if either electronic or steric effects play an important role in the binding of the aryl side chain to ANAT. Table 9 (FIG. 12) shows the effects of these substituents.

Materials and Methods

Enzyme Production and Activity Assay

Recombinant maltose-binding protein-human aspartate N-acetyltransferase (MBP-ANAT) fusion enzyme was expressed and purified as described in U.S. Provisional Patent Application No. 62/216,700. Briefly, NiCo21(DE3) competent *E. coli* cells (New England Biolabs, Ipswich, Mass.) were transformed with an MBP-ANAT-his construct and selected on LB plates with 30 µg/ml kanamycin. Colonies from these plates were used to inoculate starter cultures in LB media. After diluting each starter culture by 100-fold in 1 L of LB media, cell growth was continued for about 2 hours at 37° C. until $A_{600}$ reached 0.6. IPTG was then added to a final concentration of 0.5 mM, and protein expression was induced at 16° C. for 20 hours. To purify MBP-ANAT, a Ni Sepharose 6 Fast Flow column (GE healthcare, Pittsburgh, Pa.) was equilibrated with Buffer A (20 mM potassium phosphate, pH 7.4, 300 mM sodium chloride, 10% glycerol, and 20 mM imidazole). Cell lysate was loaded on to the column and partially purified ANAT was then eluted with a linear gradient of Buffer B (buffer A containing 400 mM imidazole). The active fractions were pooled and loaded onto an amylose column and highly purified ANAT fusion was then obtained by elution with a 0-10 mM linear maltose gradient. ANAT activity was measured by an established DTNB-based assay using a SpectraMax 190 spectrophotometer plate reader (Molecular Devices, Calif.). A typical activity assay contained 20 mM HEPES, pH 7.4, 150 mM NaCl, 5% glycerol, 40 µM DTNB, 40 µM acetyl-CoA, and 2 mM L-aspartate in a total volume of 200 µl. Reaction was monitored at 412 nm ($\varepsilon$=14.15 mM$^{-1}$ cm$^{-1}$) for at least 15 minutes.

Compound Library Screening

Three different compound libraries were used for initial screening of ANAT inhibitors. These small compound libraries were assembled in-house: an amino acids library contained 96 compounds, a metabolite library contained 96 compounds, and a second amino acids library contained 64 compounds. An additional constrained analogs library contained 77 compounds that were purchased from commercial sources. Once the dioic acid core structure was identified as a viable inhibitor of ANAT, a library of dioic acid compounds was synthesized for testing and optimization.

Procedure for the Preparation of N-Acylated Amino Acids

The general synthetic scheme for the preparation of N-acylated derivatives of aminomalonate (n=0), aspartate (n=1), glutamate (n=2), and 2-aminoadipate (n=3) is outlined in Scheme 1 (FIG. 13). The experimental conditions for the preparation of the dimethylester (2) and for the N-acylation (3) are identical to those described below and illustrated in Scheme 2 (FIG. 14).

Hydrolysis of Dimethyl-2-Amino Dioates (4)

To a mixture of dimethyl-2-amino dioate (3) (1 eq) in THF and water (9:1 ratio), sodium hydroxide (2 eq) was added and stirred for 5 to 8 h. After confirming the completion of reaction by TLC, the reaction solution was concentrated for several hours under reduced pressure to obtain the corresponding N-derivatized sodium dioates as white/light yellow solids.

Procedure for the Synthesis of Dioic Acid Derivatives

The general scheme for the production of dioic acid derivatives is illustrated in Scheme 2 for the synthesis of two N-benzoyl derivatives of L-aspartic acid (FIG. 14).

Synthesis of Dimethyl L-Aspartate Hydrochloride (6)

To an oven-dried round bottom flask, L-aspartic acid (5; 1 eq) was added and placed under a dry nitrogen gas atmosphere. The material was then dissolved in anhydrous methanol and stirred at 0° C. for a few minutes until the desired temperature was attained. Next, thionyl chloride (3 eq) was added dropwise until the reaction mixture was observed to become homogeneous, then the reaction mixture was warmed slowly to room temperature and left stirring for 14 h. The reaction mixture was then concentrated under reduced pressure to obtain compound 6 in the form of a pure white solid with no addition purification required.

Synthesis of Dimethyl Benzoyl-L-Aspartate (7)

Dimethyl L-aspartate hydrochloride (6; 1 eq) was added to a round bottom flask, to which 5 ml of dichloromethane (DCM) and 2 ml of water were added. Sodium bicarbonate (1.5 eq) was added to the resulting biphasic solution, and the reaction mixture was stirred for 2 min. Benzoyl chloride (1.4 eq) was added dropwise to this solution and the reaction mixture was stirred at room temperature overnight. After confirming completion of the reaction by TLC, the organic layer was separated and the aqueous layer was extracted three times with 50 ml of DCM. The organic extracts were combined, washed with 75 ml of brine solution (aq), dried over solid sodium sulfate, and then concentrated under reduced pressure to obtain the crude product. Silica gel column chromatography, with elution using 20% ethyl acetate in hexanes, afforded pure compound 7 as a white solid.

Synthesis of Dimethyl (3-(2,3-dihydroxyphenyl)propanoyl)-L-aspartate (8)

To a mixture of dimethyl L-aspartate hydrochloride (6; 1 eq), EDC1 (1.5 eq) and trimethylamine (1.4 eq), DCM was added and the solution stirred for 5 min. 3-phenylpropanoic acid (1 eq) was then added to this solution with stirring for 3 h. After quenching the reaction with saturated ammonium chloride, the reaction mixture was extracted thrice with ethyl acetate. The organic extracts were combined, washed with brine solution (aq), dried over solid sodium sulfate, and then concentrated under reduced pressure to obtain the crude product in the form of reddish oil. Purification was performed by silica gel column chromatography with elution using 50% ethyl acetate in hexanes to afford pure amide 8 as a yellow viscous liquid.

Preparation of N-alkyl-DL-aspartic Acid Derivatives

Various alkyl groups, where R=methyl, propyl, isopropyl, benzyl, and cyclohexyl, were coupled to the protected dimethylester of DL-aspartic acid as shown in Scheme 3 (FIG. 15).

Preparation of N-Alkyl-DL-Aspartic Acid Ester Derivatives (12)

Amine hydrochloride (0.3 mol) was added to the stirred solution of dimethyl fumarate (11) (0.2 mol) in dry pyridine (150 ml), and the reaction mixture was warmed up to 100° C. Triethylamine (0.3 mol) was added dropwise to the suspension in 3 h. When the addition was completed, the reaction mixture was stirred under reflux for 2 additional hours. The solvent was evaporated in vacuum to dryness. The residue was suspended in ethyl acetate and the mixture was neutralized with saturated sodium carbonate solution. The organic phase was separated and the aqueous phase was extracted with ethyl-acetate. The combined organic phases were washed with water, dried over sodium sulfate, and the solvent was evaporated in vacuum to give the product, as a yellowish oil. The compound was purified by flash column chromatography using 10-80% ethyl acetate:hexanes to obtain pure compound of the corresponding ester.

Preparation of N-Alkyl-DL-Aspartic Acid Derivatives (13)

Ester hydrolysis was carried out by adding 0.1 ml of $H_2O$ to a solution of N-derivatized-DL-aspartic acid esters (12) (1 eq) in THF (0.4 ml) with stirring. Then, 1 N NaOH (2 eq) was added to the reaction mixture and stirred at r. t. for 3 h. The reaction mixture was concentrated and dried for several hours under high vacuum to yield the corresponding sodium salts of the N-derivatized-DL-aspartic acids.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A compound having Formula I or Formula II:

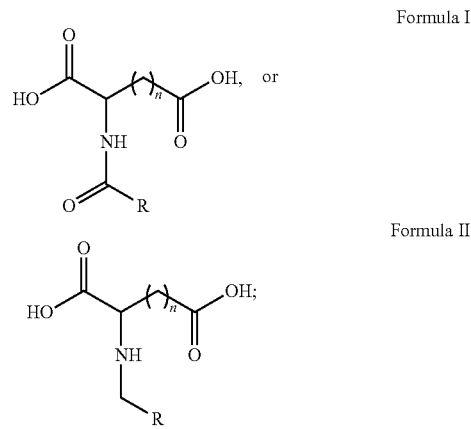

and the resulting compound inhibits aspartate N-acetyl-transferase (ANAT) activity in a brain cell and adjusts brain N-acetyl-L-aspartate (NAA) levels, wherein n is either 0 or an integer from 1 to 3, and R is a chemical moiety that permits the resulting compound to inhibit ANAT activity within brain cells, and is selected from the group consisting of:

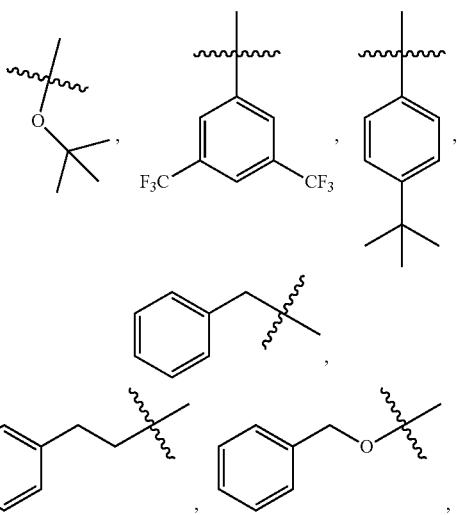

-continued

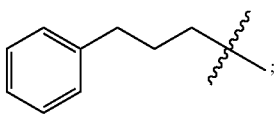

and salts, stereoisomers, prodrugs, and racemates thereof.

2. The compound of claim 1, wherein R is 3,5-(trifluoromethyl)benzene.

3. The compound of claim 1, wherein:
the compound comprises Formula I,
R is

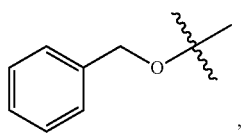 [SMILES: *OCc1ccccc1]

and n=1 or 2.

4. The compound of claim 1, wherein:
the compound comprises Formula I,
R is

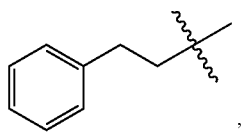 [SMILES: *CCc1ccccc1]

and n=1 or 2.

5. The compound of claim 1, wherein:
the compound comprises Formula II,
R is

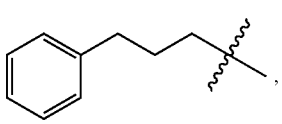 [SMILES: *CCCc1ccccc1]

and n=1.

6. The compound of claim 1, wherein the compound is selected from the group consisting of: N-carbobenzyloxy-L-glutamic acid, N-(1-oxo-3-phenylpropyl)-L-aspartic acid, N-[(benzyloxy)carbonyl]-L-aspartic acid, N-chloroacetyl-L-aspartic acid, N-(t-butoxycarbonyl)-L-aspartic acid, N-[(4-methylphenyl)sulfonyl]-L-proline, N-methyl-DL-aspartic acid, N-alanyl-L-aspartic acid, 2-(3-chloro-6-oxopyridazin-1(6H)-yl)acetic acid, isoxazole-3-carboxylic acid, and benzo[d]isoxazole-3-carboxylic acid.

7. The compound of claim 1, wherein the compound consists essentially of Formula IF1:

Formula IF1

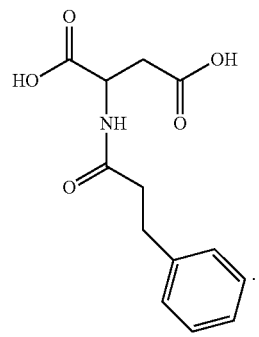

8. The compound of claim 1, wherein the compound consists essentially of Formula IF2:

Formula IF2

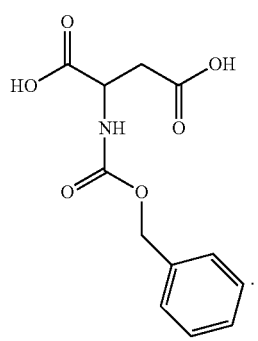

9. The compound of claim 1, wherein the compound consists essentially of Formula IG1:

Formula IG1

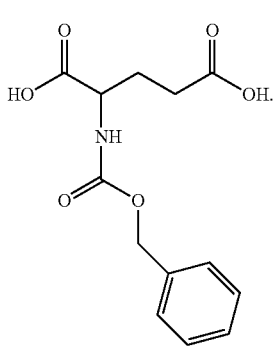

10. The compound of claim 1, wherein the compound consists essentially of Formula IG2:

Formula IG2

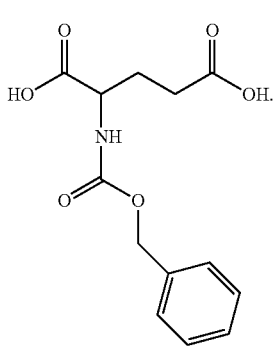

11. The compound of claim 1, wherein the compound consists essentially of Formula IIH1:
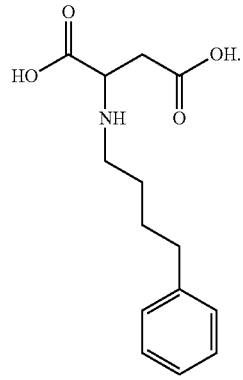
Formula IIH1
12. A pharmaceutical composition comprising:
an effective amount of a compound of claim 1; and
a pharmaceutically acceptable carrier, diluent, or adjuvant.
* * * * *